United States Patent [19]
Jones et al.

[11] Patent Number: 4,492,461
[45] Date of Patent: Jan. 8, 1985

[54] WEAR ANALYSIS EQUIPMENT

[76] Inventors: David G. Jones, P.O. Box 9531, Dharan, Saudi Arabia; Oh K. Kwon, KIST Labs., P.O. Box 131, Dongdaemum, Seoul, Rep. of Korea

[21] Appl. No.: 357,553

[22] Filed: Mar. 12, 1982

[30] Foreign Application Priority Data

Mar. 19, 1981 [GB] United Kingdom ............... 8108695

[51] Int. Cl.³ ............................................ G01N 33/28
[52] U.S. Cl. ......................................... 356/38; 73/64; 356/70
[58] Field of Search .................... 73/61 R, 64; 356/38, 356/70

[56] References Cited

U.S. PATENT DOCUMENTS

| | | | |
|---|---|---|---|
| 2,068,476 | 1/1937 | Thomas | 73/61 R |
| 2,091,222 | 8/1937 | Thomas | 356/38 |
| 3,989,381 | 11/1976 | Fulwyler | 356/39 |
| 4,047,814 | 9/1977 | Westcott | 356/70 |

Primary Examiner—Vincent P. McGraw
Attorney, Agent, or Firm—Michael J. Striker

[57] ABSTRACT

An improved method of producing a deposit of particles from a liquid medium carrier on a substrate for subsequent optical analysis of the particles, involves feeding the liquid medium carrying the particles to the substrate via a flexible tube which is not subjected to fluctuating lateral compressions. The invention has particular relevance to the making of Ferrograms from wear debris in a sample of machine lubricant.

3 Claims, 17 Drawing Figures

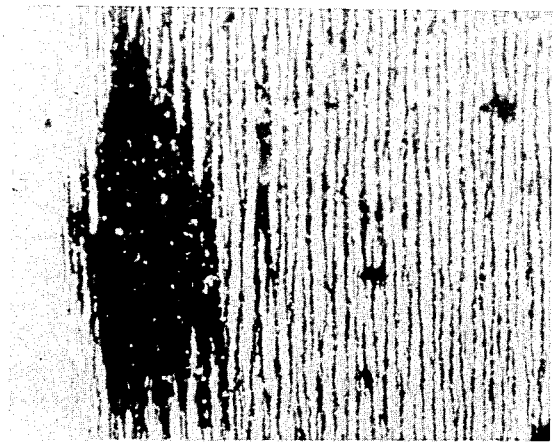
FIG.2a PARTICLES DEPOSITED IN ENTRY
REGION WHEN USING KIT 'A'
(X 100)
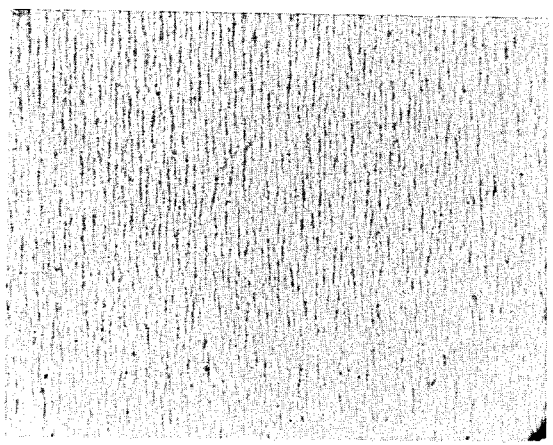
FIG.2b PARTICLES DEPOSITED AT 51mm
POSITION ON FERROGRAM
(X 100)

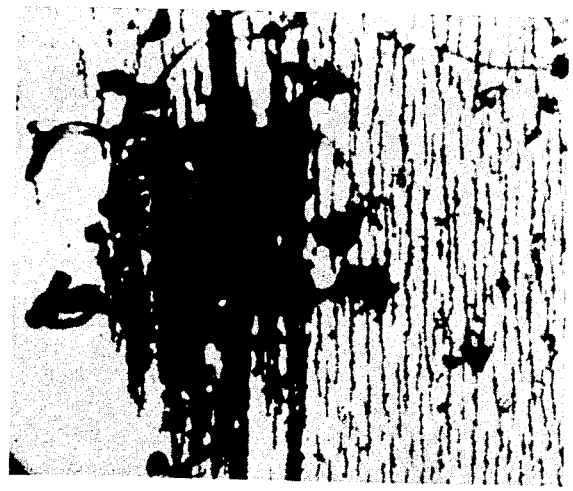
FIG. 3a  PARTICLES DEPOSITED IN ENTRY REGION WHEN USING KIT C
(X 100)
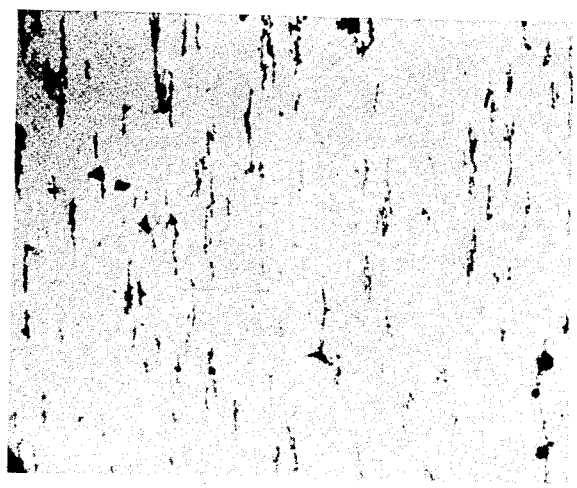
FIG. 3b  PARTICLES DEPOSITED AT 51mm POSITION ON FERROGRAM
(X 100)

FIG. 4a PARTICLES DEPOSITED BY MODIFIED
DELIVERY SYSTEM AT ENTRY (X 100)

FIG. 4b PARTICLES DEPOSITED BY MODIFIED
DELIVERY SYSTEM AT 53mm POSITION (X 100)

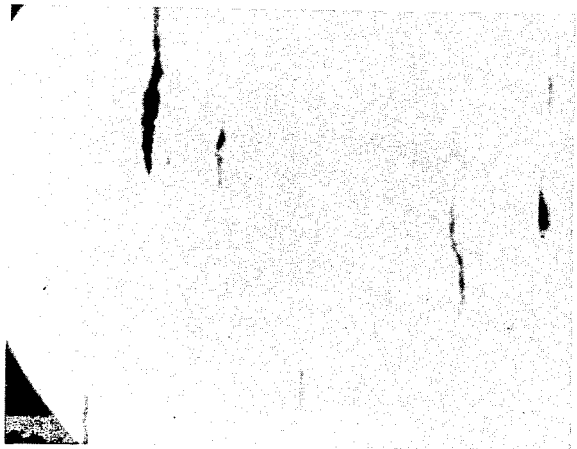
FIG.4c PARTICLES DEPOSITED BY MODIFIED
DELIVERY SYSTEM AT 51mm POSITION
(X 100)
FIG.5a ENTRAPPED EXTREMELY LONG TRICHITE
IN THE CONTACT SQUASHED PTFE TUBE
BY PUMPING.
COMMERCIAL PRODUCT "C"

FIG.5b  ENTRAPPED POLYMER-LIKE MATERIAL AND TUBULARS BROKEN. STANDARD KIT "A"
(X 100)
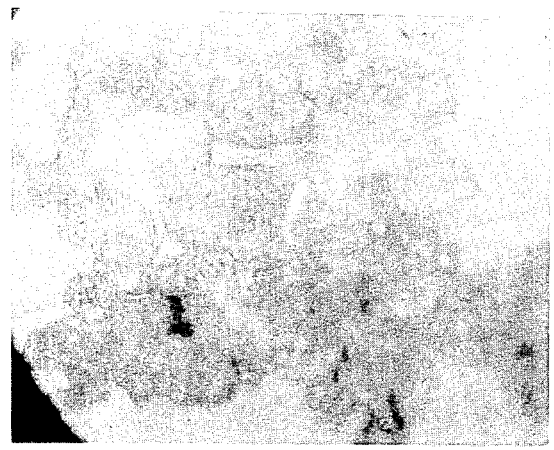
FIG.6  ENTRAPPED AND ADHERED POLYMERIC MATERIAL AND BROKEN TUBULES ON INSIDE WALL OF KIT "A" TUBE
(X 100)

FIG. 7a  INTERIOR OF DAMAGED PTFE TUBE
         DUE TO ABRASIVE ACTION OF
         WEAR PARTICLES IN KIT "A"
                                    (X 100)
FIG. 7b  INTERIOR OF DAMAGED PTFE TUBE
         DUE TO ABRASIVE ACTION OF
         WEAR PARTICLES IN KIT "C"
                                    (X 100)

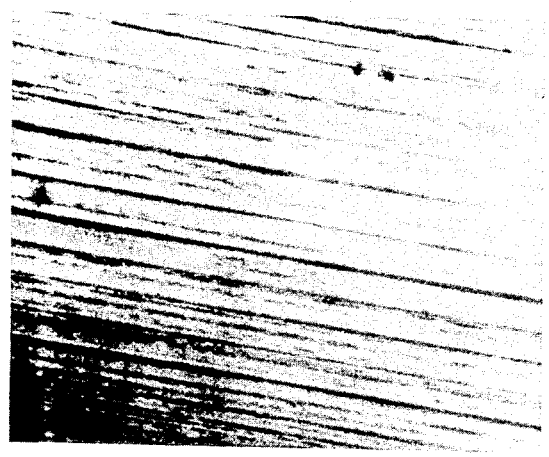
FIG. 3a  INTERIOR WALL SURFACE DAMAGE DUE TO ABRASION BY WEAR PARTICLES - COMPRESSION REGION OF TUBE OF KIT "A"
(X 100)
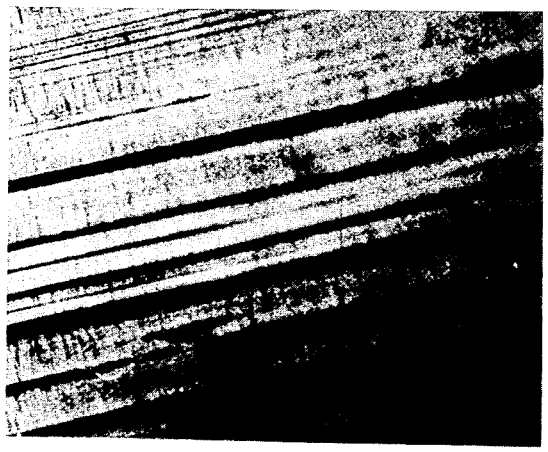
FIG. 3b  INTERIOR WALL SURFACE DAMAGE DUE TO ABRASION BY WEAR PARTICLES - COMPRESSED REGION OF TUBE OF KIT "C"
(X 100)

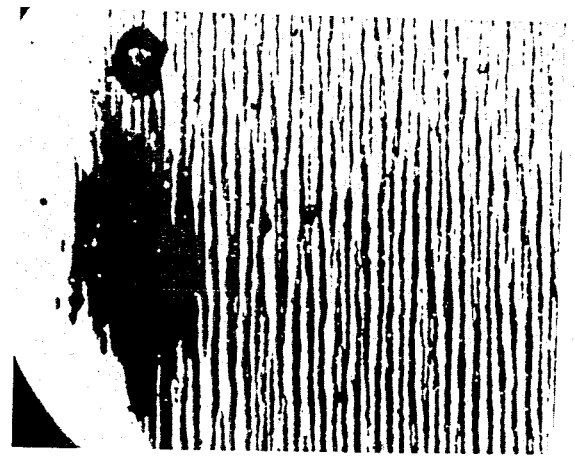
FIG. 9 PARTICLE DEPOSIT IN ENTRY REGION OF FERROGRAM WHEN USING KIT "A" PREPARED FROM SAMPLE TESTED AT 40kg, 60s run with SAE 10
(X 100)
FIG.10 PARTICLE DEPOSIT IN ENTRY REGION WHEN USING MODIFIED OIL DELIVERY SYSTEM
(X 100)

WEAR ANALYSIS EQUIPMENT

TECHNICAL FIELD

This invention relates to the method of analysing magnetically or electrically polarised or polarisable particles carried in a liquid medium and has particular reference to the optical analysis of wear debris transported in a lubricant.

It is known from U.K. Patent Specification No. 1415311 (Trans-Sonic Inc.)—which is incorporated herein by reference—to analyse wear debris in a lubricant taken from an engine or other device having relatively moving parts in order to provide qualitative and/or quantitative information regarding the wear surfaces in the engine or device. An equipment commonly used for this analysis includes a substrate (e.g. of glass) inclined slightly to the horizontal so as to be disposed in an inhomogeneous powerful magnetic field and pump means to slowly feed a diluted sample of the lubricant to an entry point at an upper part of the substrate so that the sample flows slowly down the substrate to an exit point at its lowest edge. Particles in the lubricant are retained on the substrate and are distributed therealong at varying distances from the exit point on the basis of the nature of the particles (i.e. according to size, shape and magnetic susceptibility).

The usual equipment for performing analysis of the above described type is known as a "Ferrograph" and the resultant pattern of particles as a "Ferrogram" and the science of wear particle analysis using such equipment as "Ferrography".

Information relating to the extent and severity of wear is obtained in the first instance by measuring the change in optical light density at different positions along the Ferrogram. Further analysis of the Ferrogram provides information about the nature of the wear process. The quantity of the wear debris produced can be correlated with the actual extent of the wear by measuring the concentration of the debris collected in a sample volume of the lubricant used in the test. Information about the composition and morphology of the wear particles is also relevant to the work of interpreting the nature of the wear process.

In the conventional apparatus used for producing "Ferrograms", the diluted lubricant sample is fed to the substrate using a peristaltic pump working on the sample in PTFE tubing, a fresh length of PTFE tubing being used for each sample tested.

We have now found that the fluctuating compressive forces applied to the PTFE tubing by the peristaltic pump modify the wear particles in the lubricant sample (e.g. by crushing and polishing the same) so that the population of wear particles analysed in a conventional "Ferrogram" is in many cases not the same as the population of particles in the lubricant sample drawn into the pump.

Thus the widely-used known method limits the value and extent of the interpretation relating to the nature of wear behaviour occurring in the actual system, arising from qualitative and quantitative analysis of particle deposition on the Ferrogram. Misleading information can be obtained unless a truly representative particle deposition is produced.

DISCLOSURE OF THE INVENTION

Our invention thus provides a new method for producing a "Ferrogram" which avoids any mechanical fluctuating compressive forces being applied to particles in their supply to the substrate.

Expressed in its broadest terms this invention provides a method of monitoring magnetically or electrically polarised or polarisable particles carried in a liquid medium, which method comprises passing said liquid medium with its particles carried therein through a tube, impinging a flow from said tube onto the upper surface of a substrate located in a mangetic or electric force field extending generally at right angles to said surface for attracting said particles thereonto, allowing said medium to flow across said surface and permit the force field to precipitate said particles onto the surface and optically monitoring said precipitated particles, is characterised in that said liquid medium with its particles carried therein is fed to said substrate via said tube without subjecting any region of said tube to fluctuating lateral compressions.

There are a number of different ways of securing the desired accurate dispensing of the sample liquid medium to the substrate without damaging the particles carried therein by passing them through a peristaltic pump.

For example, the liquid sample (if a lubricant, desirably admixed with a diluent) can be drawn into a length of flexible tube and a region of that tube (or another tube connected to that tube) upstream of the sample can be engaged by a peristaltic pump whereby the sample liquid is expressed onto the substrate by pumping action on fluid (e.g. air or pure diluent) upstream of the sample. Thus, a sample bottle containing diluted lubricant and suspended wear particles can be stoppered and connected to (a) a short length of tubing (e.g. PTFE tubing) which dips into the sample liquid and leads to the substrate and (b) a further air-filled tube leading to the peristaltic pump. When the pump is operating air is forced into the bottle at a controlled rate to discharge the sample liquid onto the substrate. A manually operable pressure control valve can be provided in the further tube between the pump and the bottle.

As an alternative to using a peristaltic pump acting on a fluid upstream of a liquid sample, a plunger-type pressure generator (e.g. a hypodermic syringe) can be used for the liquid sample itself or (more usually) for an upstream fluid (air or diluent).

The conventional kit supplied for making a "Ferrogram" comprises at least one substrate, a "developer" serving as a precipitation-promoting agent, and a supply of flexible tubing for carrying the developer and liquid sample to the substrate.

By adopting the method of the invention the length of flexible tubing supplied with each kit can be much shorter than heretofore (some 30 cms instead of some 70 cms in a prior art kit) and need not be of such expensive material since it no longer needs to be passed through the peristaltic pump.

Where a peristaltic pump is still employed in the method of the invention, the tubing passing through the pump need not be changed for each sample analysis and need not, therefore, be included in a sample kit.

BRIEF DESCRIPTION OF DRAWINGS

The invention will now be further discussed, by way of example, with reference to the accompanying drawings, in which:

FIGS. 2a, 2b, 3a and 3b are Ferrograms taken using conventional sample dispensing systems, FIGS. 4a, 4b and 4c are Ferrograms taken using a sample dispensing method according to the invention, FIGS. 5a, 5b and 6 are micrographs of particles trapped in the dispensing tubes by the action of the peristaltic pump in a conventional sample dispensing method, FIGS. 7a, 7b; 8a and 8b are micrographs of wear damage on the interior wall surface of tubes used in conventional sample dispensing methods, and FIGS. 9 and 10 show the entry region of two Ferrograms produced from a common sample, FIG. 9 using the prior-art dispensing system and FIG. 10 a dispensing system according to the invention.

EXPERIMENTAL WORK

Figure 1:
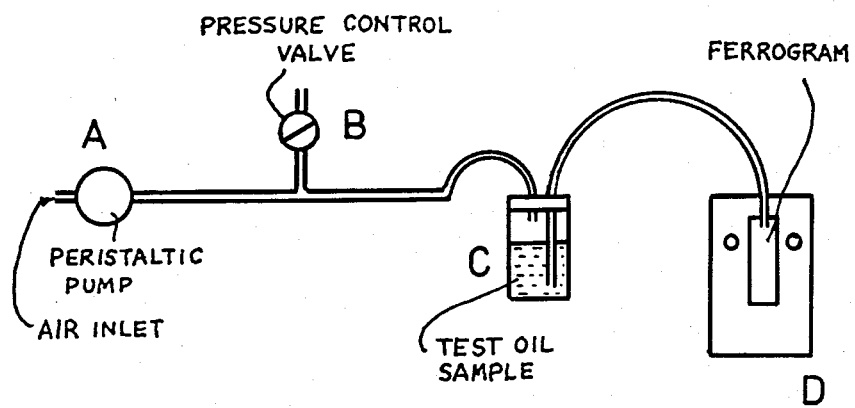
FIG. 1 is a schematic view of a modified sample dispensing system for a Ferrograph.

The oil sample for the following results was prepared in the Stanhope-Seta Four Ball machine using STANCO 90 lubricant, according to IP Test No. 239, at 70 KG-load, with a test duration of 60 seconds, using EN 31 hardened and tempered 12 mm ($\frac{1}{2}$″) balls). Each Ferrogram was prepared with 2 cc of oil sample and 3 cc of solvent fixer (tetrachloroethylene), in accordance with normal preparation procedures. The measurements of the PTFE tube used for the Ferrogram preparation are shown in Table 1.

TABLE 1

Measurments of PTFE tube dimensions.

| PTFE Tube | O.D. | Bore | Wall thickness |
|---|---|---|---|
| A | 2.375 mm | 1.689 mm | 0.343 mm |
| B | 2.337 mm | 1.727 mm | 0.305 mm |
| C | 2.184 mm | 1.575 mm | 0.305 mm |

In Table 1, PTFE tubes A and B are both standard kits supplied by the Foxboro Transonic Co., but at different times. Standard kit A is more recently supplied. Kit C is an alternative product which has a similar specification to that of the standard kit. Standard kit A and kit C were used subsequently to investigate the degradation effect on the wear particles caused by the pump action, in which the effect of using a different size PTFE tube was also examined.

To investigate further the crushing effect on wear particles, the existing oil delivery system of the Ferrograph was modified, as shown in FIG. 1, to eliminate any breaking down of the original wear particles produced during testing in the Four-Ball system. The modified oil delivery system for the Ferrogram consists of three separate units. In FIG. 1, A is a variable speed-control peristaltic pump, which can control the flow rate of air; B is an auxiliary pressure control valve; and C is a sample oil bottle from which the sample oil is delivered through the PTFE tube to the glass slide by the externally pressurized air system.

In the modified oil delivery system, the flow was fixed and controlled to deliver at three cc per minute.

Quantitative analysis of the Ferrograms prepared was undertaken in the image analysing system, Quantimet. Analysis conditions in Quantimet are as follows:

(a) Conditions at optical microscope:
Magnification
Objective lens X25 ⎫ Total magnification
⎬ microscope =
Condenser lens X6.3 ⎭ X158

(b) Location on Ferrogram:
Dense entry region
Field size .52 mm × .40 mm ⎫ Based on X158
⎬ magnification
Picture point size 1 PP = .65 mm ⎭ at microscope (c) Conditions in Quantimet:
Detection
Ferrous free-metal particles - reflected light with green filter, detecting for particles lighter than background.
Measurements

| Area covered | A(PP): a measure of particle concentration. |
|---|---|
| Total intercept | I(PP). |
| Particle count | Based on chord width dimension and counting particles greater than 1 PP in increasing steps of 1 PP until zero count is registered. |

N.B:
(1) Full feature count system was used for all measurements.
(2) Measurements was made at 90° orientation of microscope head.
(3) Data was recorded manually.
(4) PP represents Picture Point - the unit of measurement in a detected feature. It is of equal height and width and it may be considered as a unit of linear or area measurement.

Initial examination of each Ferrogram was undertaken with an optical microscope. The PTFE tubes subjected to squeezing action by the peristaltic pump were investigated in the optical microscope in reflected and transmitted light at X100 optical magnification, after cutting the tubes axially (see FIGS. 5a and 5b).

RESULTS AND DISCUSSION

According to normal preparation procedures, Ferrograms were prepared by using standard kit A and kit C in Table 1, from the 2 cc oil sample tested in the Four-Ball machine at 70 KG, for 60 seconds, with STANCO 90 lubricant.

FIGS. 2a and 2b show wear particles deposition on the Ferrogram in the dense entry region and 51 mm position, respectively, using standard kit A.

In FIG. 2a, few PTFE particles were in evidence. Most free-metal particles deposited in the dense entry are smaller in size, viz. ≦1.5 μm. In this region, a heavy deposition of black coke-covered-like metal particles are clearly in evidence. FIG. 2b shows very heavy deposition of sub-micron 'metal dust' particles. Most of the sub-micron particles deposited in the 51 mm region are covered with black carbonaceous material (coke), and this results in minimum reflection from reflective light in the optical microscope.

FIGS. 3a and 3b show typical particle deposition of the Ferrogram prepared by using commercial kit C in the regions corresponding with those of FIGS. 2a and 2b, respectively. The particle deposition in both locations shown in FIGS. 3a and 3b indicates that the number and concentration of wear particles deposited were reduced when compared with those of FIGS. 2a and 2b. However, in FIG. 3a it is noticeable that the polymer-like materials, viz. trichite, chunky glassy flakes, and also PTFE debris, are much increased and heavily deposited in the dense entry region. Most of the larger particles deposited in the dense entry region were not detectable by reflected light in Quantimet, because of superficial deposits of black-coke material on wear debris, or similar types of metal matrix mixtures. Particles deposited at the 51 mm position in FIG. 3b exhibit similar features to those of FIG. 3a, but are much smaller in size. FIGS. 4a, 4b and 4c show typical particle depositions along a slide which was prepared with a similar oil sample but using the modified oil delivery system shown in FIG. 1. All along the slide, e.g. in the dense entry region (FIG. 4a), at 53 mm (FIG. 4b), and at 51 mm (FIG. 4c), very few sub-micron wear particles are evident. It is clear from FIGS. 4a-4c that most of the original wear particles generated from the Four-Ball machine are very heavy chunky particles, as seen in FIGS. 4a and 4b. The black carbonaceous deposit present on the surface of the wear particles is the same as that observed in FIGS. 2a, 2b and 3a, 3b. Due to the carbonaceous material deposit on the wear particles of FIG. 4a, when the particles were subjected to analysis in Quantimet by reflected light, the number and size of the heavy chunky particles were much reduced from the actual deposition, because the image analyser was only measuring reflecting particles. The phenomenon of carbonaceous material deposit on wear particles requires attention before further study of quantitative wear analysis can continue, especially when using the Quantimet system. This phenomenon has been studied recently, and confirmed by the authors, in a research programme related to concentrated lubricated sliding contacts in the Four-Ball scuffing machine. The effect of carbon deposit on wear particles is very significantly increased in the post-transition region of the Four-Ball machine scuffing results, due to active thermal decomposition of lubricant at the sliding contact.

A recent paper by T. E. Cranshaw and R. G. Campany (A.E.R.E., Harwell) reports similar evidence of carbon deposit occurring on wear surfaces, when tested in a David Brown Two-Disc machine. According to their results, it is shown by Mössbauer Spectroscopy that, in some cases, the increase of carbon content (atomic %) on scored surfaces is as much as 15%. The concluded with the suggestion that breakdown of the lubricant had occurred in the scoring phase of the test.

In FIGS. 4a, 4b and 4c, polymer-like materials, e.g. trichite, tubule, and also chunky glassy flakes were deposited on the Ferrogram, but no PTFE debris were found. FIG. 5a shows an extremely long trichite entrapped inside the commercial kit C tube after preparing the Ferrogram, but no chunky glassy polymer materials were observed. FIG. 5b shows several broken pieces of trichite or tubule entrapped and adhered on the inside wall of standard kit A tube, after the test had been conducted. Many chunky glassy polymer materials were also in evidence trapped inside the tube. FIG. 6 shows a different location on the inside wall of standard kit A tube, wherein very heavy glassy polymer material is entrapped and adhered on the inside wall, mixed together with broken pieces of trichite.

FIGS. 7a and 7b show typical cutting abrasive wear scars on the inside wall of the PTFE tube disposed within the peristaltic pump. By examination in an optical microscope, it is evident that, in the case of standard kit A and commercial product C, most damage by cutting abrasive wear has occurred at a position just before the flattened section of tubing caused by the action of the pump. It is clear that the original wear particles transported through the tube tend to become attached to the inside wall of the PTFE tube. This is a direct result of the constricting action of the pump, causing a narrowing of the tube clearance. This also causes cutting-type abrasive wear on the inside wall from any sharp, hard edges on the wear particles.

FIGS. 8a and 8b also show typical abrasive wear tracks on the inside walls of standard kit A and commercial product C, respectively. It is also seen that numerous tiny cracks have formed perpendicular to the abrasive wear tracks. These may have resulted from fatigue deformation of the PTFE tube due to the cyclic stress effect of the peristaltic pump.

QUANTITATIVE ANALYSIS OF FERROGRAMS

Based on techniques developed previously for quantitative analysis of the wear particle size distribution on a Ferrogram, the results of Quantimet analysis are tabulated in Table 2. Sample 1 is the Ferrogram prepared by using standard kit A; sample 2 for commercial product C; and sample 3 by the modified oil delivery system.

TABLE 2

| Quantimet Analysis of Particle Distribution Effect of Pumping Action | | |
|---|---|---|
| Kit A Standard Procedure Sample 1 | Kit C Standard Procedure Sample 2 | Modified delivery system Sample 3 |
| A (PP)    3165 | 1000 | 3136 |
| I (PP)     914 | 222 | 417 |
| P (PP)   3650 | 832 | 1436 |
| N 1 PP     60 | 5 | 12 |
| N 2 PP    106 | 9 | 19 |

| (PP) | Particle count (N) | (PP) | Particle Count (N) | (PP) | Particle count (N) |
|---|---|---|---|---|---|
| >1 | 681 | 1 | 36 | 1 | 37 |
| 2 | 139 | 2 | 33 | 2 | 29 |
| 3 | 101 | 3 | 25 | 3 | 25 |
| 4 | 71 | 4 | 16 | 4 | 19 |
| 5 | 47 | 5 | 12 | 5 | 17 |
| 6 | 33 | 6 | 11 | 6 | 16 |
| 7 | 22 | 7 | 10 | 7 | 16 |
| 8 | 11 | 8 | 7 | 8 | 13 |
| 9 | 7 | 9 | 6 | 9 | 9 |
| 10 | 5 | 10 | 3 | 10 | 8 |
| 11 | 4 | 11 | 3 | 12 | 7 |
| 12 | 3 | 12 | 2 | 13 | 6 |
| 13 | 2 | 13 | 2 | 16 | 5 |
| 16 | 1 | 14 | 1 | 18 | 4 |
| 26 | 1 | 15 | 1 | 22 | 3 |
| 27 | 0 | 16 | 0 | 23 | 1 |
|  |  |  |  | 42 | 1 |
|  |  |  |  | 43 | 0 |

The particle count of Sample 1 is much larger than the counts obtained for Samples 2 and 3.

Moreover, the majority of the particles (about 80% of particles greater than 1 PP) were $\leq 1.5$ μm in size. This indicates that the wear particles were actively broken down from their original size. The greater the tube diameter or wall thickness, the more the wear particles were reground to a smaller size and, simultaneously subjected to a polishing effect. The smaller particle deposit of Sample 2 is a clear indication of the reduced compressive effect by the pump when using the smaller diameter tube or a thinner wall thickness from that of standard kit A. Another reason for the lower particle count in Sample 2 (when detecting lighter than the background with reflected light) is that the polishing effect on wear particles was not as pronounced as with Sample 1.

The heavy polymer material deposit in the dense entry region of the Ferrogram (see FIG. 3a) tends to obscure the free-metal particle count in Quantimet by the reflected light. However, about 58% of total particle population analysed belong to the size range of 1.5 μm to 5 μm (Table 2). The results obtained from the analysis of Sample 3 show the particle distribution obtained for non-degraded wear particles. In general, the size of the particles is much greater than those of Samples 1 and 2. This is more clearly evident from the optical microscope examination, as seen in FIGS. 4a and 4b. The overlapping of the large chunky particles which caused the out-of-focus problem in the optical microscope, coupled with the heavy carbon deposit on the large wear particles, were the main reasons for the marked reduction in size and number of the wear particles in the deposition measured by Quantimet (Sample 3; Table 2). The former can be resolved by proper sample dilution.

CONCLUSIONS

The results that have been obtained during the preliminary phase of our investigation have proved to be most informative. The evidence obtained has provided relevant information concerning the nature of the problems associated with the use of the existing Ferrography machine. The results obtained are summarised as follows:

(1) In the course of preparing a Ferrogram using the existing system, the original wear particles are degraded mechanically by the oil delivery system due to the compressive squeezing effect of the peristaltic pump action.

(2) The greater the PTFE tube diameter or wall thickness, the more the wear particles were degraded. This was accompanied by a polishing action which served to remove the original outer layers (e.g. oxides). Brittle particles were shattered in the process.

(3) Polymer material and also some glassy type materials were found to be trapped and adhered to the inside wall of the PTFE tube, particularly at the position where the tube was subjected to squeezing action by the pump.

(4) Severe cutting abrasive wear marks were formed on the inside wall of the PTFE tube by the transported wear particles. Fatigue cracks formed by plastic deformations, perpendicular to the abrasive wear tracks, were produced on the inside wall of the PTFE tube.

(5) The effect of regrinding and other forms of wear particle degradation during the preparation will markedly influence the qualitative and quantitative analysis of wear particles. By modifying the sample supply method according to the invention the particles are deposited on the Ferrogram without experiencing degradation.

What is claimed is:

1. A method of analyzing magnetically polarisable wear particles carried in a liquid medium, comprising the steps of:

passing the liquid medium with its wear particles carried therein from a reservoir thereof through a length of a tube to an outlet end thereof;

impinging a flow from the outlet end onto an entry point on a upper surface of a substrate located in a magnetic force field having a component extending generally at right angles to the upper surface for attracting the particles thereonto, the liquid medium with its wear particles carried therein being fed to the entry point on the substrate via said length of the tube by applying pressure to the reservoir of the liquid medium with its wear particles without subjecting any region of said length of the tube to fluctuating lateral compressions;

allowing the medium to flow from the entry point across the upper surface while the force field precipitates the particles in any array on the upper surface at varying distances from the entry point depending on the nature of the wear particles; and optically monitoring the array of precipitated particles.

2. A method as claimed in claim 1, in which the sample of liquid medium with its wear particles carried therein is expelled from the reservoir by a peristaltic pump operating on a further tube upstream of the reservoir, which further tube contains a medium which is void of the wear particles for analysis.

3. A method as claimed in claim 1, in which a plunger-type pressure generator is used to expel the liquid medium with its wear particles carried therein from the reservoir.

* * * * *